United States Patent [19]

Grenner et al.

[11] Patent Number: 5,051,237
[45] Date of Patent: Sep. 24, 1991

[54] LIQUID TRANSPORT SYSTEM

[75] Inventors: Gerd Grenner, Lincoln; Shai Inbar, Boston; Ernest W. Long, Concord, all of Mass.

[73] Assignee: P B Diagnostic Systems, Inc., Westwood, Mass.

[21] Appl. No.: 210,732

[22] Filed: Jun. 23, 1988

[51] Int. Cl.$^5$ .............................................. G01N 31/22
[52] U.S. Cl. ........................................ 422/56; 422/57; 422/58; 422/102; 436/169; 436/170
[58] Field of Search ................. 422/56, 57, 58, 102; 436/169, 170

[56] References Cited

U.S. PATENT DOCUMENTS

| | | | |
|---|---|---|---|
| 4,002,056 | 1/1977 | Kopito | 73/53 |
| 4,233,029 | 11/1980 | Columbus | 23/230 R |
| 4,254,083 | 3/1981 | Columbus | 422/55 |
| 4,271,119 | 6/1981 | Columbus | 422/50 |
| 4,302,313 | 11/1981 | Columbus | 204/195 R |
| 4,310,399 | 1/1982 | Columbus | 204/195 R |
| 4,323,536 | 4/1982 | Columbus | 422/56 |
| 4,413,407 | 11/1983 | Columbus | 28/825 |
| 4,426,451 | 1/1984 | Columbus | 436/518 |
| 4,439,526 | 3/1984 | Columbus | 436/180 |
| 4,549,952 | 10/1985 | Columbus | 204/416 |

Primary Examiner—Robert J. Warden
Assistant Examiner—Jill Johnston
Attorney, Agent, or Firm—Gaetano D. Maccarone

[57] ABSTRACT

A liquid transport system provides controlled flow of liquid in a liquid flow zone between two surfaces wherein one surface includes a plurality of projections, or raised areas, arranged substantially throughout the surface in the liquid flow zone and an aperture for allowing the introduction of liquid between the two surfaces. In a preferred embodiment the projections on the first surface are arranged in parallel spaced rows and parallel spaced columns. The second surface may be one surface of a layer of a diagnostic assay element.

12 Claims, 1 Drawing Sheet

LIQUID TRANSPORT SYSTEM

BACKGROUND OF THE INVENTION

Fluid delivery systems which are capable of providing a controlled flow of liquid between two surfaces are required for various applications. One such application is the field of biological diagnostic assay devices for the rapid analysis of analytes which are present in biological fluids. Various types of such assay elements are known in the art. Generally, a sample of a biological fluid, e.g., plasma, serum, etc., is applied to the assay element and as a result of the interaction between an analyte of interest in the sample fluid and the reagent(s) present in the assay element a detectable change corresponding to the presence of the analyte is brought about. The detectable change can be a color change which may be evaluated visually or read spectrophotometrically such as with a densitometer. In another scheme based on the presence of fluorescent-labeled biological species a fluorescent output signal is generated and read spectrofluorometrically. In order to obtain accurate and reproducible results it is essential that the sample fluid be distributed uniformly throughout the assay element so that a uniform signal or color is provided for reading by the instrument.

Various techniques have been described in the art for uniformly distributing a sample fluid throughout an assay element. It is known, for example, to use for this purpose fibrous layers, woven cloth layers, membranes having substantially uniform porosity and uniformly porous layers which allow capillary migration to provide the uniform fluid distribution. Also, there are known techniques for distributing liquids between two surfaces by the use of capillary action and such techniques have been taught for use in conjunction with providing small amounts of a sample fluid to analytical assay elements. U.S. Pat. No. 4,323,536 discloses a diagnostic test device which includes a plurality of test elements each of which is supplied with sample liquid from a single liquid sample. The device comprises a first member, a second covering member, these members having opposing surfaces, and means for spacing the members apart a distance effective to induce capillary flow of liquid introduced between the surfaces and thus create a liquid transport zone. One or both of the surfaces may have a plurality of exposed grooves in order to control the liquid flow paths in the device. U.S. Pat. No. 4,233,029 discloses a similar liquid transport device which has a controlled capillary liquid flow zone.

The prior art liquid transport devices are not satisfactory in all instances. For example, in filling such small spaces with liquid there is often encountered a problem with forming undesired pockets of trapped air which can cause errors in the case of quantitative analysis of the sample liquid. Accordingly, there is a continuing need for liquid transport devices It is therefore an object of this invention to provide a liquid transport system.

Another object is to provide a liquid transport system capable of efficiently controlling the flow of a liquid between two opposing surfaces A further object of the invention is to provide a liquid transport system for providing a uniform distribution of a liquid sample to a biological diagnostic assay device.

Yet another object of the invention is to provide a diagnostic assay device for the rapid analysis of a fluid sample.

BRIEF SUMMARY OF THE INVENTION

These and other objects and advantages are accomplished in accordance with the invention by providing a liquid transport device comprising first and second members having opposed surfaces which are spaced apart a distance which will permit capillary flow of a liquid throughout a liquid flow zone defined by some part of, or the entire opposed surfaces. The surface of the first member opposed to the surface of the second member carries a plurality of projections, or raised areas, which are in contact or virtual contact with the opposed surface of the second member and arranged substantially throughout the surface in the desired liquid flow zone. The projections function to control the flow of liquid between the opposed surfaces in the liquid flow zone. In a preferred embodiment the projections carried by the surface of the first member are arranged in an ordered pattern of parallel spaced rows and columns which extend along both dimensions of the plane of the surface to provide a liquid flow which is substantially uniform in the liquid flow zone. The liquid transport device also includes an opening, such as an aperture extending through the first member, to permit a liquid to be introduced into the liquid flow zone.

In operation, a liquid is introduced into the liquid flow zone such as by being dropped from a pipette through an aperture in the first member. When the liquid contacts the opposing surfaces of the first and second members the projections carried by the opposed first surface serve to provide a controlled flow of the liquid in the liquid flow zone. It is necessary that the liquid contact the opposed surface of the second member in order for the liquid flow to begin. This condition can be ensured by various techniques. In one embodiment an aperture in the first member can be relatively large and the liquid can be introduced directly onto the opposed surface of the second member. In embodiments where the aperture is relatively small a wick of absorbent material may be disposed in the aperture to conduct the liquid into contact with the opposed surface of the second member or the first member can include one or more small liquid directing elements extending from the periphery of the aperture into contact or virtual contact with the opposed surface of the second member.

In a preferred embodiment the second member comprises a biological diagnostic assay element and the liquid transport system provides a uniform distribution of sample liquid across the opposed surface of the assay element. In this manner there is obtained a uniform concentration of the sample fluid throughout the area of the assay element which will be analyzed. The detectable change in the assay element, whether it is a color change which is to be evaluated visually or read out spectrophotometrically or whether it is some other type of change such as the generation of a fluorescent output signal which is to be read out spectrofluorometrically, will be analyzed over a specific portion of the assay element surface, typically a circular or rectangular area in the center of the test element. Thus, it is essential to obtain a uniform distribution of the test fluid throughout the area of the test element which will be analyzed.

In a particularly preferred embodiment the diagnostic assay element incorporated in the assay device is a thin film multilayer test element. The controlled liquid flow characteristics of the device are particularly well suited for use with thin film multilayer diagnostic test elements because the volume delivered is very small and controlled very precisely which matches the requirements of such test elements. Thus, there is provided to the surface of the assay element a uniformly distributed, small volume of precisely metered sample fluid. A further advantage is that the sample fluid is not exposed very much to the ambient environment after being delivered to the diagnostic test element and therefore any evaporation of any significance which could lead to a change in the analyte concentration is prevented or at least greatly minimized.

BRIEF DESCRIPTION OF THE DRAWINGS

For a better understanding of the invention as well as other objects and further features thereof, reference is made to the following detailed description of various preferred embodiments thereof taken in conjunction with the accompanying drawing wherein.

DESCRIPTION OF THE PREFERRED EMBODIMENTS

Figure 1:
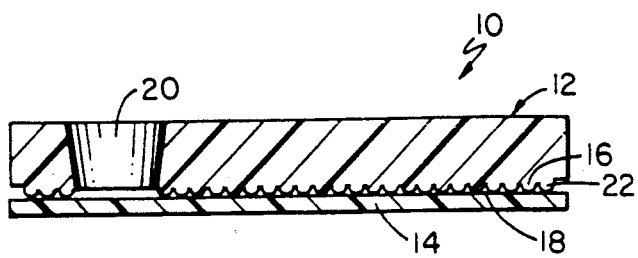
FIG. 1 is a partially schematic cross-sectional view of a liquid transport device according to the invention.

Referring now to FIG. 1 there is seen a preferred embodiment of a liquid transport device according to the invention. It should be noted that the thickness of the device has been magnified for ease of illustration; the actual preferred devices of the invention are relatively thin, having a typical thickness in the range of from about 2 to about 10 mm. The device 10 includes a first member 12 and a second member 14, either of which may be transparent or opaque, having opposed surfaces 16 and 18 respectively. First member 12 includes an aperture 20 which is in fluid communication with the liquid flow zone defined by opposing surfaces 16 and 18 to allow a sample fluid to be introduced thereinto. Surface 16 of first member 12 carries a plurality of projections 22 which provide a controlled flow of the fluid throughout the liquid flow zone. The projections 22 may be in contact with surface 18 as shown in FIG. 1 or in virtual contact, that is, spaced slightly apart from the surface.

It should be noted here that although the device 10 has been illustrated with a flat planar configuration, which is preferred, the device may comprise any two generally parallel first and second members which are spaced apart a capillary distance so as to permit capillary flow of a liquid between them. The respective members may be curvilinear, for example.

Figure 2:
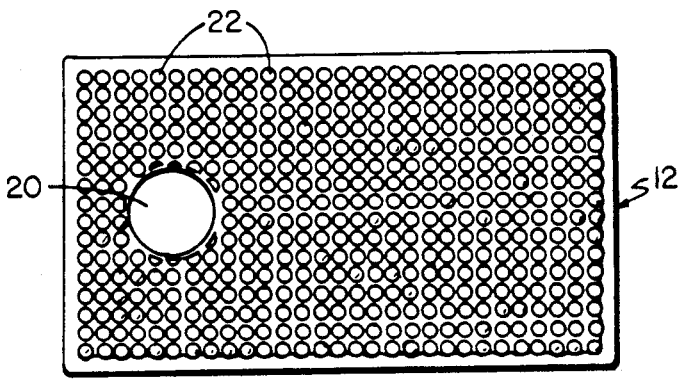
FIG. 2 is a partially schematic top view of surface 16 of first member 12 of FIG. 1.

The projections 22 are arranged substantially throughout the surface 16 coextensive with the area for which controlled flow of the liquid is desired. As seen in FIGS. 1 and 2 the projections are arranged substantially throughout the entire surface 16 so that the liquid flow zone is substantially coextensive with the dimensions of first and second members 12 and 14, respectively. The spreading of the fluid is a function of the gap between opposed surfaces 16 and 18, the contact angle, i.e., the "wettability" of the opposed surfaces 16 and 18, and the viscosity of the fluid. Generally, the opposed surfaces 16 and 18 are spaced apart a capillary distance, i.e., a distance which will allow capillary forces to draw the liquid into the gap and permit the liquid to flow throughout the liquid flow zone. Since capillary flow is a function of the surface tension of the meniscus of the liquid between the two surfaces, it is apparent that the distance between the two surfaces will vary for different types of liquids. The distance between opposing surfaces 16 and 18 is generally in the order of from about 50 to about 150 microns or more.

As noted previously, the projections 22 may be in virtual contact or in contact with surface 18. In a preferred embodiment of the invention the projections 22 are utilized to define the gap between the opposed surfaces 16 and 18 in addition to providing the controlled liquid flow. In this embodiment a sufficient number of projections 22 will be in contact with surface 18 to define the gap between surfaces 16 and 18. Further it is desirable in the preferred embodiments of the invention that the gap between opposing surfaces 16 and 18 in the liquid flow zone be substantially uniform. When the projections 22 are used to define a substantially uniform gap generally a major amount, i.e , about 50% or more, should be in contact with surface 18. Further, in this embodiment it is preferred that about 75% or more and particularly preferred that substantially all, that is, about 95% or more, of the projections 22 be arranged in contact with surface 18. The height of projections 22 is generally in the range of from about 50 to about 150 microns or more and the preferred height is from about 80 to about 120 microns.

In a preferred embodiment the projections 22 are arranged in ordered rows and columns extending substantially along both dimensions of surface 16 as illustrated in FIG. 2. By arranging the projections in this manner there is provided a substantially linear liquid front during spreading which can avoid the creation of air bubbles during the liquid flow.

The aperture 20 may be of any size and configuration. The aperture may be large enough to permit the fluid sample, which may be a droplet having a volume of about 8 to 10 $\mu l$, to contact surface 18 without touching the sides of the aperture. Of course the volume of the sample depends on the type of liquid involved, e.g., aqueous or non-aqueous, and the device application. However, in preferred embodiments it is desired to have an aperture which is as small as possible in order to minimize any evaporation of the liquid sample. The shape of aperture 20 may be circular with the same diameter throughout or, as shown in FIG. 1, the diameter may become progressively smaller from the top to the bottom surfaces of member 12.

The first member 12 may be transparent or opaque and may be made from any suitable material including synthetic, film-forming polymeric materials such as, for example, polyvinylacetate, polyvinylchloride, polyvinylchloride-polyvinylalcohol copolymers, polypropylene, polystyrene, cellulose acetate butyrate, hydrolyzed cellulose acetate butyrate, styrene acrylonitrile and the like, metals, ceramics, etc. The surface 16 of the material may be treated such as by hydrolysis or with an additive which causes its surface to be more easily wetted by the fluid. Proteins such as gelatins and albumins as well as surfactants are suitable for this purpose. Some metals and polymeric materials strongly absorb proteins and the contact angles of liquids applied thereto are changed significantly. Polystyrene and hydrolyzed cellulose acetate butyrate are preferred materials. First member 12 including aperture 20 and projections 22 can be made by various techniques including injection molding.

As noted previously it is preferred to arrange the projections 22 on surface 16 in parallel spaced rows and columns extending substantially along both dimensions of the plane of surface 16, as illustrated in FIG. 2. The spacing of the projections is dependent upon the type of liquid sample involved and the device application. In a preferred embodiment wherein the device is used for a diagnostic assay for a biological fluid, e.g., plasma or serum, it is typically rectangular, with typical dimensions of about 7 by 10 mm in width and length. It has been found to be preferred in this embodiment to arrange the projections 22 apart in the range of from about 0.25 mm to about 0.4 mm on centers. It has been found that excellent spreading of plasma or serum samples can be obtained in a rectangular 7×10 mm device with 25 columns along the longer dimension and 37 rows along the shorter dimension. It is preferred, as illustrated in FIGS. 1 and 2 to have the aperture 20 off-centered since it has been found that more uniform spreading of the liquid in the liquid flow zone can be obtained in this manner.

The projections 22 may be various shapes such as convex, trapezoidal or v-shaped. The choice of the shape in any particular instance is dependent in part upon the device application. For example, in a biological diagnostic assay device it is desirable to have as little as possible of the surface of the assay element covered by contact with the projections so that a uniform concentration of the sample fluid can be applied across the element. Thus, in assay devices where the projections are used to define the gap it is preferred to use v-shaped projections or conical projections with a very slightly rounded tip.

Figure 3:
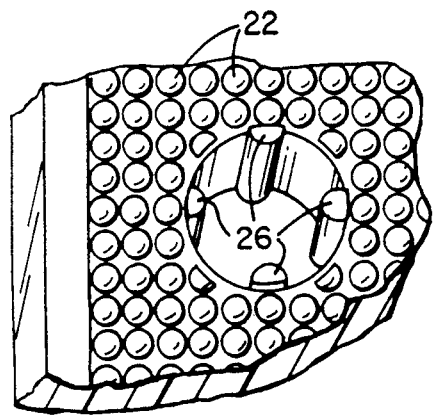
FIG. 3 is a partially schematic fragmentary perspective view of another embodiment of a first member of a liquid transport device.

A capillary break 24 (see FIG. 5) may be disposed in the devices according to the invention. The capillary break assists in confining the sample liquid to the liquid flow zone defined by projections 22. As noted previously, in the case of diagnostic assay devices it is desirable to have an aperture 20 which is as small as possible in order to minimize any evaporation of the sample fluid during the assay procedure. For 8-10 μl samples of plasma or serum it has been found that an aperture diameter of about 2 mm is satisfactory to minimize undesired evaporation of the sample. Depending upon the manner in which the sample is introduced into the aperture, e.g., from a pipette, etc., there may result in certain situations a condition wherein the liquid, because of surface tension effects, etc., remains in the aperture and does not contact surface 18 so as to be drawn into the liquid flow zone. In one embodiment a wick of an absorbent material can be arranged in the aperture to ensure that the liquid sample is brought into contact with surface 18 and subsequently drawn into the liquid flow zone. The bottom surface of the wick may be in actual contact with surface 18 or spaced slightly apart therefrom. In another embodiment one or more small liquid directing elements can be arranged to extend from the periphery of aperture 20 into the liquid flow zone As is the case with the absorbent wick, the liquid directing elements can be in contact or virtual contact with surface 18. FIG. 3 illustrates one embodiment wherein four liquid directing elements 26 are arranged in the aperture The first element 12, including the aperture 20, projections 22 and liquid directing elements 26 can be formed in one step such as by an injection molding procedure in the case of polymeric film forming materials.

Figure 4:
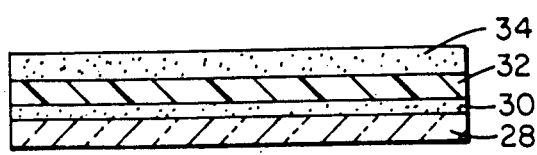
FIG. 4 is a partially schematic, cross-sectional view of a multilayer assay element.

In the diagnostic assay devices of the invention the second element 14 may comprise any diagnostic assay element whether a single layer or multilayer. A typical thin film assay element has a thickness of about 0.1 mm and comprises one or more reagent layers residing on a support layer which can be transparent or opaque. The assay element may include various other layers as are known in the art including, for example, a light-blocking layer to permit the signal-generating species in one layer to be read out without interference from materials present in another layer, a registration layer for holding a signal generating species formed in, or released from, another layer, etc. FIG. 4 illustrates a preferred embodiment of the assay element incorporated in the assay device of the invention. The assay element comprises a transparent support 28 carrying reagent layer 30, light blocking layer 32 and optional layer 34 which may be a reagent layer, a protein filter layer, an anti-abrasion layer etc. In one embodiment reagent layer 30 comprises an immunocomplex of a fluorescent-labeled antigen and an antibody directed against the antigen. In this embodiment the antibody is immobilized in layer 30 such as by being covalently bound to the surface of support layer 28 or to a matrix material or by being physically held by the matrix material. The matrix material may be a nonporous hydrophilic gel material such as gelatin, a polysaccharide, a derivatized polysaccharide, including mixtures thereof, or the like. Light blocking layer 30 may comprise any suitable material such as for example, iron oxide, titanium dioxide or the like dispersed in a binder material such as agarose. Optional layer 34 comprises an antiabrasion layer of a material such as a polysaccharide in the embodiment where an immunocomplex is present in reagent layer 30. Layer 34 can be omitted where the immunocomplex is present in reagent layer 30. In an alternate embodiment a fluorescent-labeled antigen is dispersed in layer 34 and layer 30 includes the immobilized antibody. In practice, the fluid sample is introduced into the aperture 20 of the first member and is spread uniformly across the surface of the assay element by the projections 22. Accordingly, a uniform concentration of any analyte present in the sample is distributed across the assay element and the liquid diffuses throughout layers 30, 32 and 34 as well as filling the liquid flow zone between the surface of layer 34 and the surface 16 of first member 10 and an equilibrium is established. When present, the sample analyte, in this illustrative discussion an antigen of interest, will compete with the fluorescent-labeled antigen (the same antigen as the sample antigen or an analogue thereof) for the available binding sites on the antibody. In the instance where the fluorescent-labeled antigen is complexed originally to the antibody in layer 30, the former will be dissociated therefrom and replaced by the sample antigen in a ratio approximately equal to the relative amounts of sample antigen and fluorescent-labeled antigen. Where the fluorescent-labeled antigen is originally present in upper layer 34 it will be diffused into layer 30 along with the liquid sample and compete with the sample antigen for the binding sites on the immobilized antibody. Thus, in each embodiment, depending upon the amount of antigen present in the sample, some percentage of the fluorescent-labeled antigen will bind to those immobilized antibodies which are not bound to the sample antigen. The remainder of the labeled antigen will be distributed throughout the remainder of the device, i.e., throughout layers 32, and 34 and the liquid flow zone between the surface of layer 34 and the opposed surface 16 of first member 12. The amount of labeled antigen bound to the immobilized antibodies in reagent layer 30 at any time is inversely proportional to the amount of sample antigen. A quantitative determination of the sample antigen is obtained by irradiating the immobilized antibody layer through the transparent base with appropriate excitation energy. Since the immobilized antibody layer 30 is very thin in comparison to the combined thickness of layers 32 and 34 and the liquid flow zone, i.e., a ratio of from about 1:20 to about 1:100, and because light-blocking layer 32 prevents any of the excitation energy from entering layer 34 or the liquid flow zone, the optical readout system will measure the amount of labeled antigen which is bound to the immobilized antibody and a very small percentage of the free labeled antigen which is distributed throughout the remainder of the device. As noted previously the readout signal is inversely proportional to the amount of the sample antigen, that is, as the amount of sample antigen increases the signal decreases.

Figure 5:
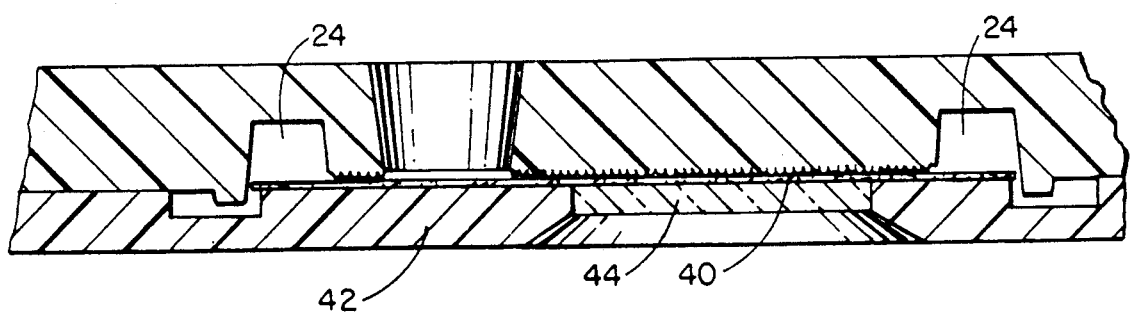
FIG. 5 is a partially schematic, cross-sectional view of a diagnostic assay device according to the invention.

In commercial use the diagnostic assay device of the invention preferably is used with an automated test apparatus which performs the analysis automatically and records the result. In such test apparatus the diagnostic assay device is typically mounted in a holder which could be an integral part of the apparatus. Where the assay device is of a flat planar configuration and it is used in an automated test apparatus it will be appreciated that the area of the device which is read should be a fixed distance from the optical readout system. This condition can be ensured by various techniques. FIG. 5 illustrates an embodiment of an assay device wherein the assay element 40 is held in a flat position by means of support member 42 which may be made of a polymeric film-forming material. Support member 42, which may be transparent or opaque, includes a transparent window area 44 through which the signal developed in the assay element can be read out by the optical system.

The invention will now be described further in detail with respect to specific prepared embodiments by way of examples it being understood that these are intended to be illustrative only and the invention is not limited to the material, conditions, apparatus, or process parameters, etc., recited therein.

EXAMPLE I

An assay element was prepared comprising a transparent subcoated polyethylene terephthalate photographic film base upon which there are coated in succession the following layers:

1. a reagent layer comprising 10 mg/m² of a 1:1 immunocomplex of a rhodamine fluorescent-labeled theophylline represented by the formula

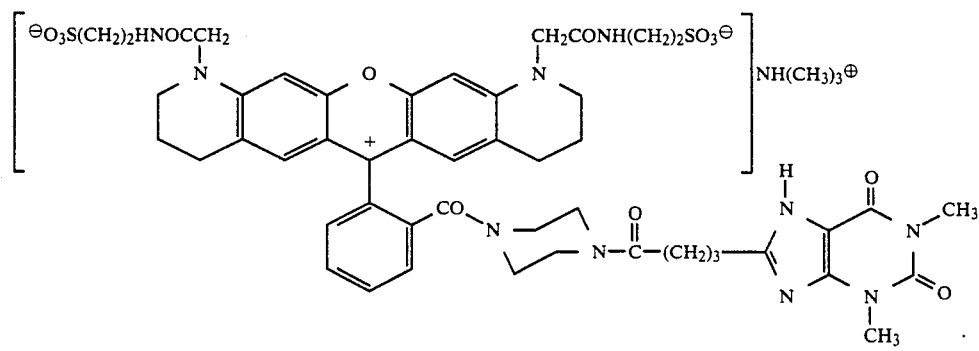

and a monoclonal theophylline antibody (commercially available from Kallestad Diagnostics, Austin, Texas); and a buffer in 500 mg/m² of a nonporous hydrophilic gel matrix material comprised of a blend of a polysaccharide and a derivatized polysaccharide;

2. a light blocking layer comprising 6000 mg/m² of iron oxide, 180 mg/m² of Tween 20 ®, a surfactant available from Rohm and Haas Co., and a buffer in 2000 mg/m² of a polysaccharide.

3. a layer comprising 372 mg/m² ethylene diamine tetraacetic acid, 40 mg/m² of phenoxynaphthalene sulfonic acid, 180 mg/m² of Tween 20 and a buffer in 2000 mg/m² of a polysaccharide.

The assay element was incorporated into a multilayer assay device according to the invention by combining it with a layer carrying projections on a surface thereof as illustrated in FIG. 1. The liquid spreading layer comprised a 7×10 mm opaque polystyrene layer which included an aperture and carried on the surface thereof opposed to the top surface of the assay element, an ordered array of about 60 micron high projections arranged in 25 columns of 38.

The multilayer assay device was heated at 37° C. for three minutes and a sample having a known amount of theophylline was then applied to the device. The device was then incubated at 37° C. for six minutes, after which it was irradiated with 550 nm excitation energy from a xenon lamp. The fluorescent emission signal was read at 580 nm and recorded. Samples with varying amounts of theophylline were assayed in this manner. The results obtained are shown in Table I.

TABLE I

| Theophylline (μg/ml) | Signal (Volts) |
|---|---|
| 2.50 | 3.153 |
| 5.00 | 2.770 |
| 10.00 | 2.305 |
| 20.00 | 1.801 |
| 40.00 | 1.205 |

It can be seen that the signal intensity decreased as the amount of theophylline in the sample increased thereby showing that the assay device operated in the intended manner.

EXAMPLE II

Theophylline was added to a sample of pooled human serum at a concentration of about 5.0 μg/ml. A droplet of the sample was added to an assay device as described in Example I and the assay conducted in the manner described therein. The assay was repeated with twelve different assay devices. The mean reading for the twelve samples was 2.76 volts ±0.036 volt (1.3% coefficient of variation). A theophylline concentration of 5.05±0.030 μG/ml(5.9% CV) was obtained by fitting the signal to the standard curve obtained from the data shown in Table I. This result shows the assay device according to the invention to be both accurate and precise. It should also be noted that no specific precaution was taken to prevent evaporation of fluid from the assay device during processing.

Although the invention has been described with respect to specific preferred embodiments it is not intended to be limited thereto but rather those skilled in the art will recognize that variations and modifications may be made therein which are within the spirit of the invention and the scope of the appended claims.

What is claimed is:

1. A diagnostic assay device comprising a first member and a diagnostic assay element, said first member and said assay element having opposed surfaces which are spaced apart throughout an intended liquid transport zone a distance effective to cause capillary flow of a sample liquid introduced therebetween throughout the intended liquid transport zone and means to permit introduction of a liquid between the opposed surfaces of said first member and said assay element, said opposed surface of said first member carrying a plurality of discrete noncontinuous projections arranged throughout said surface in the intended liquid transport zone, each said projection being spaced apart from the others in a predetermined pattern and being in contact or virtual contact with said opposed surface of said assay element.

2. The diagnostic assay device as defined in claim 1 wherein said projections are arranged in an ordered pattern of parallel spaced rows and parallel spaced columns.

3. The diagnostic assay element as defined in claim 1 wherein said projections are from about 50 to about 150 microns in height.

4. The diagnostic assay element as defined in claim 1 wherein said first member comprises a material which is impervious to the liquid to be assayed.

5. The diagnostic assay device as defined in claim 1 wherein said means to permit introduction of liquid comprises an aperture in said first member.

6. The diagnostic assay device as defined in claim 1 further including at least one liquid directing element extending from said aperture into contact or virtual contact with said opposed surface of said assay element.

7. The diagnostic assay device as defined in claim 5 wherein said diagnostic assay element comprises at least one reagent layer carried by a support.

8. The diagnostic assay device as defined in claims 7 wherein said support is transparent to wavelengths of radiation which are utilized to obtain a signal which is a function of an analyte in a liquid sample.

9. The diagnostic assay device as defined in claim 8 wherein said diagnostic assay element comprises a support carrying a reagent layer which in turn carries a light blocking layer.

10. The diagnostic assay device as defined in claim 9 wherein said reagent layer comprises an immunocomplex of a labeled analyte complexed to an immobilized binding partner.

11. The diagnostic assay device as defined in claim 10 wherein said label is a fluorescent moiety.

12. The diagnostic assay device as defined in claim 1 wherein said diagnostic asssay element comprises at least one reagent layer carried by a support.

* * * * *

UNITED STATES PATENT AND TRADEMARK OFFICE
CERTIFICATE OF CORRECTION

PATENT NO. : 5,051,237

DATED : September 24, 1991

INVENTOR(S) : Gerd Grenner, Shai Inbar and Ernest W. Long

It is certified that error appears in the above-identified patent and that said Letters Patent is hereby corrected as shown below:

Col. 10, claim 8, line 1, delete "claims" and insert --claim--.

Signed and Sealed this

Third Day of August, 1993

Attest:

MICHAEL K. KIRK

Attesting Officer

Acting Commissioner of Patents and Trademarks